(12) United States Patent
Yin et al.

(10) Patent No.: US 7,713,749 B2
(45) Date of Patent: May 11, 2010

(54) SUBSTRATE FOR FABRICATING PROTEIN MICROARRAYS

(75) Inventors: Li Te Yin, Taipei (TW); Chao Yun Tsao, Taipei (TW); Chung We Pan, Pingtung (TW); Su Fung Chiou, Keelung (TW); Zheng Cheng Chen, Changhua County (TW)

(73) Assignee: Industrial Technology Research Institute, Hsinchu (TW)

( * ) Notice: Subject to any disclaimer, the term of this patent is extended or adjusted under 35 U.S.C. 154(b) by 456 days.

(21) Appl. No.: 10/959,296

(22) Filed: Oct. 7, 2004

(65) Prior Publication Data

US 2005/0100969 A1 May 12, 2005

(30) Foreign Application Priority Data

Nov. 12, 2003 (TW) .............................. 92131659 A

(51) Int. Cl.
*G01N 33/543* (2006.01)

(52) U.S. Cl. .................. 436/518; 436/532; 436/528; 436/529; 436/530; 436/524; 435/7.1; 435/283.1; 435/287.2; 422/50; 422/55; 422/68.1

(58) Field of Classification Search ................. 436/518, 436/532, 528, 529, 530, 524; 435/7.1, 283.1, 435/287.2; 422/50, 55, 68.1
See application file for complete search history.

(56) References Cited

U.S. PATENT DOCUMENTS

| | | | | |
|---|---|---|---|---|
| 4,137,382 A | * | 1/1979 | Vetter, Jr. | 528/271 |
| 5,716,825 A | * | 2/1998 | Hancock et al. | 435/286.5 |
| 5,837,466 A | * | 11/1998 | Lane et al. | 435/6 |
| 5,989,692 A | * | 11/1999 | Brown | 428/215 |
| 6,703,491 B1 | * | 3/2004 | Homburger et al. | 536/23.1 |
| 6,734,012 B2 | * | 5/2004 | Andreoli et al. | 435/287.1 |
| 2005/0026215 A1 | * | 2/2005 | Predki et al. | 435/7.1 |
| 2005/0053973 A1 | * | 3/2005 | Kolkman et al. | 435/6 |
| 2006/0270064 A1 | * | 11/2006 | Gordon et al. | 436/518 |

* cited by examiner

*Primary Examiner*—Melanie J. Yu
(74) *Attorney, Agent, or Firm*—Bacon & Thomas, PLLC

(57) ABSTRACT

The present invention provides a substrate for protein microarrays, whereby compound A and GPTS are mixed for coating onto a solid support to form a layer, wherein said compound A is selected from a group consisting of nitrocellulose, poly(styrene-co-maleic anhydride) and polyvinylidene fluoride. Moreover, the present invention also provides a protein microarray by depositing proteins on said layer of said substrate.

14 Claims, 4 Drawing Sheets

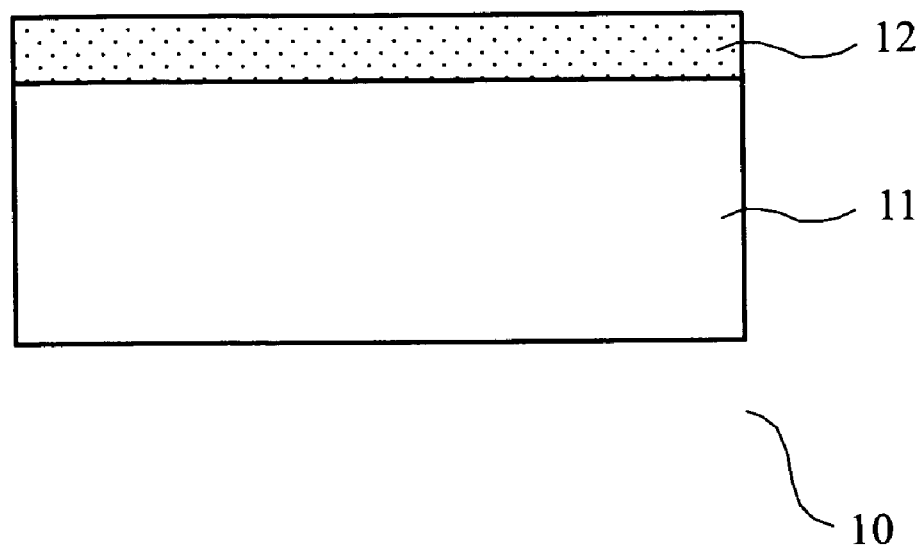
FIG. 1
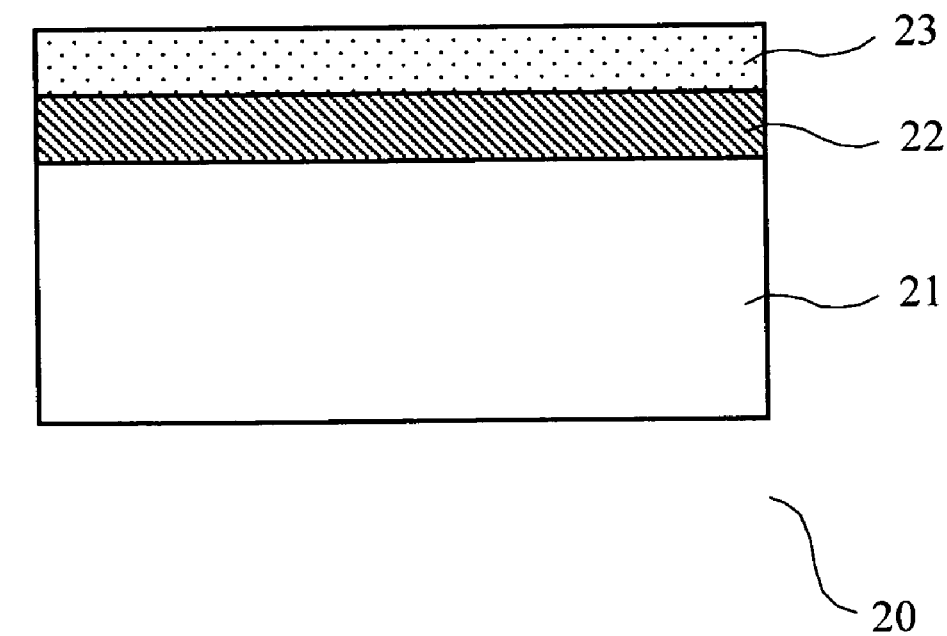
Prior Art  FIG. 2

SUBSTRATE FOR FABRICATING PROTEIN MICROARRAYS

BACKGROUND OF THE INVENTION

1. Field of the Invention

The present invention discloses a substrate for fabricating protein microarrays.

2. Description of Related Art

Microarray technology has become a crucial tool for large-scale and high-throughput biology. It allows fast, easy and parallel detection of thousands of addressable elements in a single experiment. In the past few years, protein microarray technology has shown its great potential in basic research, diagnostics and drug discovery. It has been applied to analyze antibody-antigen, protein-protein, protein-nucleic-acid, protein-lipid and protein-small-molecule interactions, as well as enzyme-substrate interactions. Recent progress in the field of protein microarrays includes surface chemistry, capture molecule attachment, protein labeling and detection methods, high-throughput protein/antibody production, and applications to analyze entire proteomes.

Efficient immobilization of protein is a key factor in determining the overall success of a microarray. If the immobilized probes are not correctly oriented on the microarray surface or are denatured, it can dramatically affect the downstream protein interaction events. Therefore, the selection of substrate material and its surface treatment pose a big challenge in the manufacturing of protein chips. Conventional treatment of substrate for protein microarray involves a dual-layer modification process, where the modified substrate contains a buffer layer and a reaction layer. The buffer layer serves to connect the substrate and the reaction layer, where one end of the buffer compound may react with the substrate and the other end may react with the reaction layer to help immobilize the reaction layer on the substrate. The reaction layer comprises compound having the function of protein-capture agent, which can immobilize protein on the reaction layer and furthermore on the substrate through the buffer layer.

The conventional process for modification of protein microarrays substrate consists of at least two modification steps, which are time consuming and run the risks of resulting in uneven modified surface, residual solvent and protein denaturation caused by reactants.

SUMMARY OF THE INVENTION

The present invention provides a substrate for immobilizing protein. The substrate comprises a solid support having a surface, and a layer coated on said surface of said solid support, said layer comprising a 3-glycidoxypropyltrimethyoxysilane (GPTS) and a compound A, wherein said compound A is selected from a group consisting of nitrocellulose, poly(styrene-co-maleic anhydride) (PSMA), and polyvinylidene fluoride (PVDF). The substrate is suited for protein microarrays.

In accordance with the present invention, said solid support may be quartz, glass, plastic, silicon or polymer. The mixing ratio of aforesaid compound A to 3-glycidoxypropyltrimethoxysilane is 9~24:1, preferably 24:1.

The aforesaid compound A is preferably nitrocellulose.

The present invention also provides a protein microarray, comprising a solid support having a surface, a layer coated on said surface of said solid support, said layer comprising a 3-glycidoxypropyltrimethyoxysilane (GPTS) and a compound A, and a protein deposited onto said layer, wherein said compound A is selected from a group consisting of nitrocellulose, poly(styrene-co-maleic anhydride) (PSMA), and polyvinylidene fluoride (PVDF).

The present invention provides a protein microarray characterized in that the adhesion of compound A to microarray substrate is strengthened through the chemical bonding between the silane group in GPTS and the substrate without the aid of a buffer layer as required in conventional process before proceeding with subsequent steps of protein immobilization.

BRIEF DESCRIPTION OF THE DRAWINGS

FIG. 1 shows the schematic diagram of a protein microarray substrate in single-step process according to the present invention.

FIG. 2 shows the schematic diagram of a protein microarray substrate manufactured in a conventional manner.

DETAILED DESCRIPTION OF THE INVENTION

Figure 3:
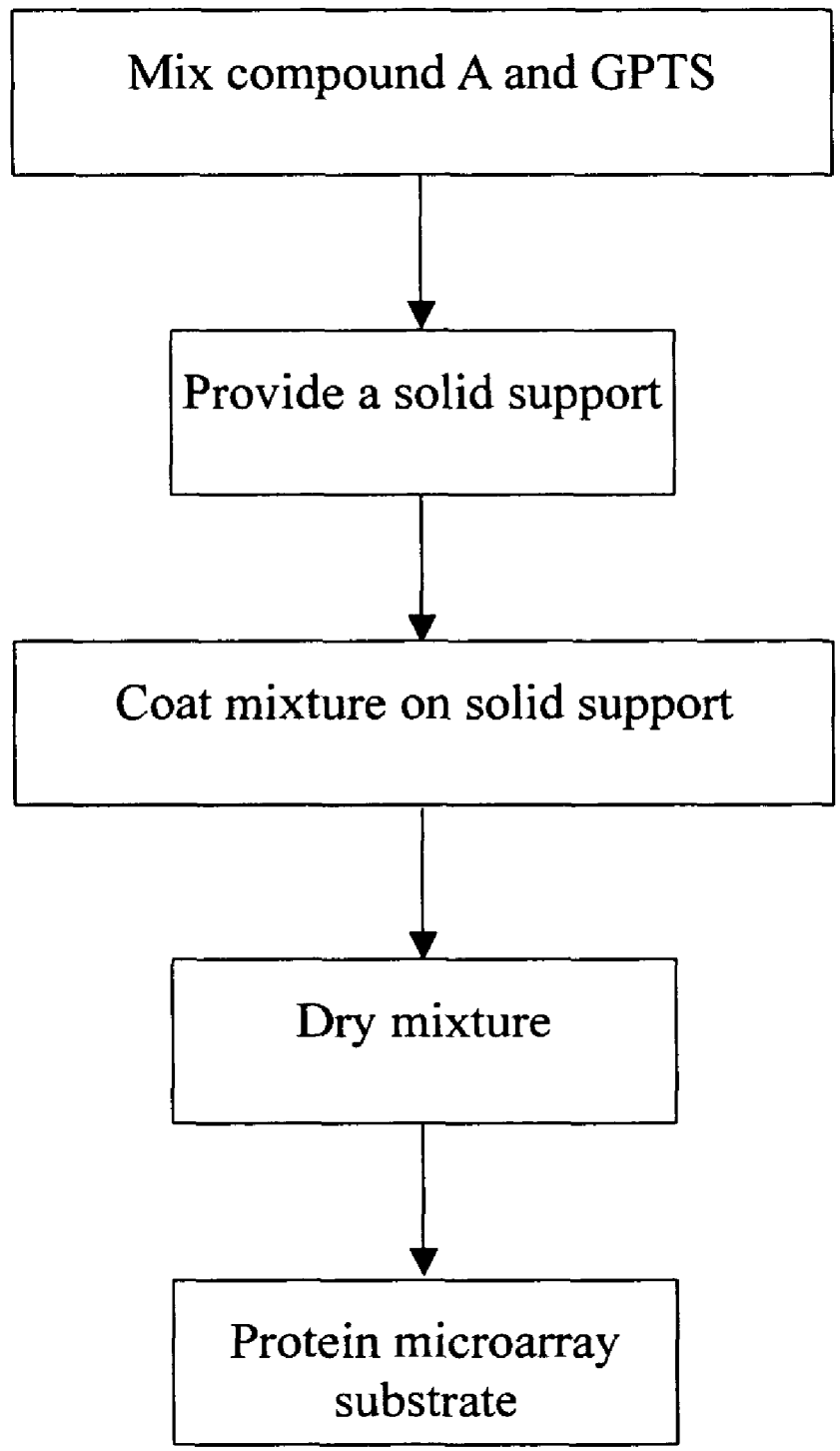
FIG. 3 shows the flow chart of method for manufacturing substrate for protein microarrays in single-step process according to the present invention.

The implementation and features of the method and substrate for protein microarrays by single-step manufacturing process provided herein are described below.

The term "solid support" used herein refers to any suitable materials with solid surfaces, which include, but not limited to, quartz, glass, silicon or polymer.

The term "substrate" used herein refers to a solid support that is treated/coated with chemicals such that it is capable of binding biomolecules.

The term "protein" used herein refers to a polymer of amino acid residues. The proteins immobilized on the array of the invention may be antibodys, antigens, receptors, ligands or enzymes.

As shown in FIG. 1, the protein microarray substrate 10 manufactured in single-step process provided by the present invention comprises a solid support 11; and a layer 12, which is coated onto said solid support 11 for depositing biomolecules.

The material of the solid support 11 may be quartz, glass, plastic, silicon or polymer.

The composition of the layer 12 comprises compound A and GPTS; wherein said compound A is selected from a group consisting of nitrocellulose, poly(styrene-co-maleic anhydride) (PSMA), and polyvinylidene fluoride (PVDF). The function of GTPS is to promote the adhesion of compound A to the surface of said solid support 11 through the chemical bonding between the silane group of GPTS and said solid support 11. Accordingly, the protein depositing on said solid support 11 may proceed without an extra buffer layer between the interface of the solid support 11 and said layer 12.

The mixing ratio of aforesaid compound A to GPTS is 9~24:1, preferably 24:1.

The aforesaid compound A is preferably nitrocellulose (NC); wherein the mixing ratio of nitrocellulose to GPTS is preferably 24:1.

FIG. 2 shows a conventional protein microarray substrate 20, which consists of a solid support 21; a buffer layer 22 coated on said solid support 21; and a reaction layer 23 coated on said buffer layer 22 for depositing proteins; wherein a buffer layer 22 is present to promote the adhesion of reaction layer 23 on said solid support 21. As compared to the protein microarray substrate 10 produced in a single-step process as shown in FIG. 1, the conventional protein microarray substrate 20 needs an additional step of making a buffer layer 22.

In an example of the present invention, the layer 12 was prepared by mixing nitrocellulose and GPTS, wherein nitrocellulose can adsorb proteins and GPTS replaces the buffer layer by directly coating on the surface of the solid support after mixing with nitrocellulose. The chemical bonding between the silane groups of GPTS and the surface of the solid support 11 increases the adhesion between the nitrocellulose and the surface of the solid support 11 without the need of a buffer layer to help adhere nitrocellulose on the solid support 11.

FIG. 3 depicts the flow chart of the method for manufacturing a substrate for a protein microarray according to the present invention, comprising the steps of mixing compound A and GPTS to form a mixture, wherein said compound A is selected from a group consisting of nitrocellulose, PSMA and PVDF, preferably nitrocellulose; providing a solid support made of quartz, glass, plastic, silicon or polymer; coating said mixture onto said solid support by means of spin coating or other coating methods; and finally drying (preferably under the conditions of 60° C., 2 hours) the mixture on said solid support to produce a protein microarray substrate.

Figure 4:
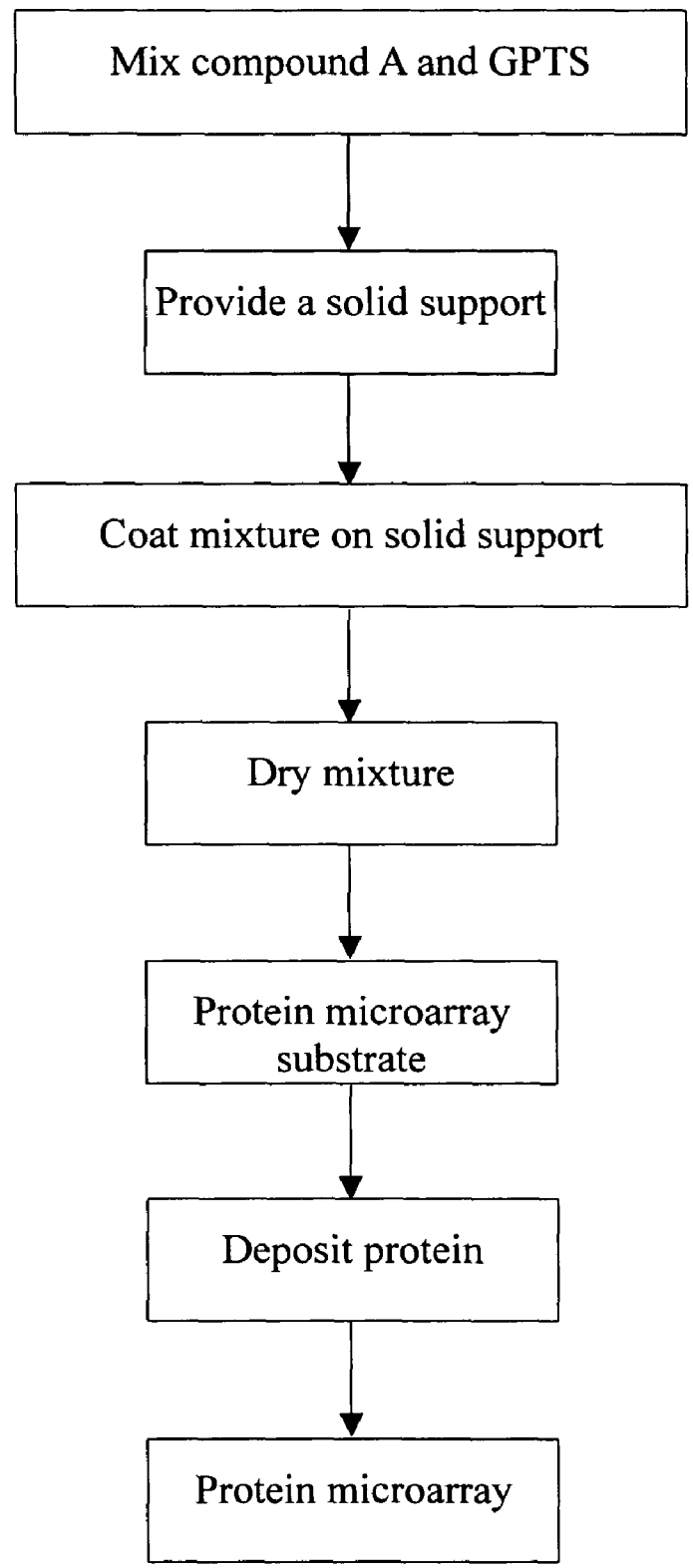
FIG. 4 shows the flow chart of method for fabricating protein microarrays in single-step process according to the present invention.

FIG. 4 depicts the flow chart of the method for fabricating protein microarray according to the present invention, comprising the steps of mixing compound A and GPTS to form a mixture, wherein said compound A is selected from a group consisting of nitrocellulose, PSMA and PVDF, preferably nitrocellulose; providing a solid support made of quartz, glass, plastic, silicon or polymer; coating said mixture onto said solid support by means of spin coating or other coating methods; drying (preferably under the conditions of 60° C., 2 hours) the mixture on said solid support to produce a protein microarray substrate; and depositing biomolecules on said coated substrate to produce a protein microarray; wherein said biomolecules comprise antibody, antigen, receptor, ligand, or enzyme.

The implementation results of manufacturing protein microarray substrate using single-step process are presented with the illustration of an example.

EXAMPLE

In this example, protein microarray substrate 10 shows in FIG. 1 was produced according to the process shown in FIG. 3, which comprises the following steps: first mix nitrocellulose with GPTS in the ratio of 24:1 to form a mixture; take a piece of solid support made of glass; spin coat aforesaid mixture onto the glass solid support at the speed of 500 r.p.m for 10 seconds and then 1000 r.p.m for 20 seconds; dry the mixture coated on said solid support for 2 hours under 60° C. to produce a protein microarray substrate.

After depositing streptavidin-cy5 (SA-cy5) diluted in 1 time, 10 times and 100 times respectively onto the protein microarray substrate produced above, compare the signal intensity from the substrate and from conventional dual-layer microarray substrate using epoxy resin as buffer layer and nitrocellulose as reaction layer (glass/epoxy resin/nitrocellulose).

Figure 5:
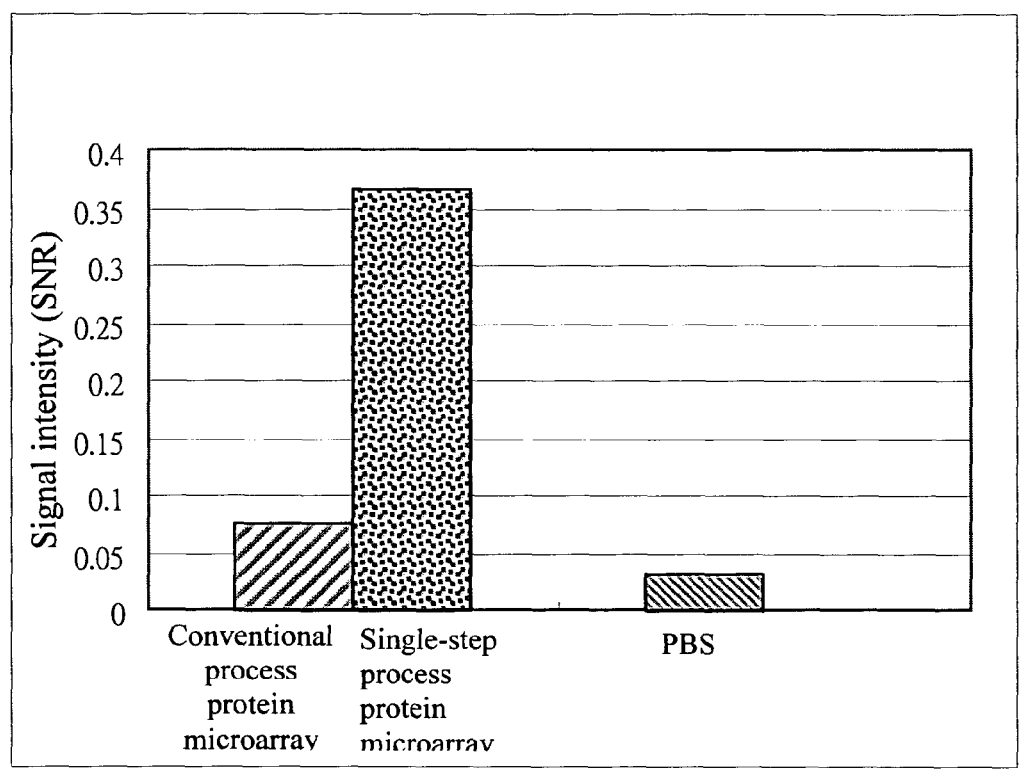
FIG. 5 shows the comparison of signal intensity from single-layer protein microarray according to the present invention and conventional dual-layer protein microarray applied in detection of antigen.

Finally use the SA-cy5 bound microarray in antigen assay. The assay results from conventional protein mircroarray and the protein microarray provided herein as shown in FIG. 5 indicate that the signal intensity of the microarray provided herein was much higher than that of conventional microarray, demonstrating that the protein microarray produced using single-step process according to this invention can effectively increase the sensitivity in protein detection.

What is claimed is:

1. A substrate for fabricating protein microarrays consisting of:
    a solid support having a surface; and
    a layer coated on said surface of said solid support, said layer consisting of a mixture of 3-glycidoxypropyltrimethyoxysilane (GPTS) and a compound A, wherein said compound A is selected from the group consisting of nitrocellulose and poly(styrene-co-maleic anhydride).

2. The substrate for fabricating protein microarrays according to claim 1, wherein the material of said solid support is quartz, glass, plastic, silicon or polymer.

3. The substrate for fabricating protein microarrays according to claim 1, wherein the mixing ratio of compound A to 3-glycidoxypropyltrimethoxysilane is 9~24:1.

4. The substrate for fabricating protein microarrays according to claim 3, wherein the mixing ratio of compound A to 3-glycidoxypropyltrimethoxysilane is 24:1.

5. The substrate for fabricating protein microarrays according to claim 1, wherein said compound A is nitrocellulose.

6. The substrate for fabricating protein microarrays according to claim 1, wherein the mixing ratio of nitrocellulose to 3-glycidoxypropyltrimethyoxysilane is 24:1.

7. A protein microarray consisting of:
    a solid support having a surface;
    a layer coated on said surface of said solid support, the composition of said layer consisting of a 3-glycidoxypropyltrimethyoxysilane (GPTS) and a compound A, wherein said compound A is selected from the group consisting of nitrocellulose and poly(styrene-co-maleic anhydride); and
    a protein deposited on said layer.

8. The protein microarray according to claim 7, wherein the material of said solid support is quartz, glass, plastic, silicon or polymer.

9. The protein microarray according to claim 7, wherein the mixing ratio of compound A to 3-glycidoxypropyltrimethoxysilane is 9~24:1.

10. The protein microarray according to claim 9, wherein the mixing ratio of compound A to 3-glycidoxypropyltrimethoxysilane is 24:1.

11. The protein microarray according to claim 7, wherein said compound A is nitrocellulose.

12. The protein microarray according to claim 7, wherein the mixing ratio of nitrocellulose to 3-glycidoxypropyltrimethyoxysilane is 24:1.

13. The substrate for fabricating protein microarrays according to claim 1, wherein there is no buffer layer between the surface of the substrate and the coated layer.

14. The protein microarray according to claim 7, wherein there is no buffer layer between the surface of the substrate and the coated layer.

* * * * *